(12) United States Patent
Morimoto (10) Patent No.: US 9,097,749 B2
(45) Date of Patent: Aug. 4, 2015

(54) DIFFERENTIAL TRANSFORMER TYPE MAGNETIC SENSOR AND IMAGE FORMING APPARATUS

(71) Applicant: KYOCERA Document Solutions Inc., Osaka (JP)

(72) Inventor: Masashi Morimoto, Osaka (JP)

(73) Assignee: KYOCERA Document Solutions Inc., Osaka (JP)

( * ) Notice: Subject to any disclaimer, the term of this patent is extended or adjusted under 35 U.S.C. 154(b) by 56 days.

(21) Appl. No.: 14/054,299

(22) Filed: Oct. 15, 2013

(65) Prior Publication Data

US 2014/0103922 A1    Apr. 17, 2014

(30) Foreign Application Priority Data

Oct. 17, 2012    (JP) .................................. 2012-229499

(51) Int. Cl.
  *G01R 33/028* (2006.01)
  *H01F 27/28* (2006.01)
  *G01N 27/72* (2006.01)
  *G03G 15/08* (2006.01)

(52) U.S. Cl.
  CPC .............. *G01R 33/028* (2013.01); *G01N 27/72* (2013.01); *G03G 15/0853* (2013.01)

(58) Field of Classification Search
  CPC .................................................. G01R 33/028
  USPC ........................................................ 324/258
  See application file for complete search history.

(56) References Cited

U.S. PATENT DOCUMENTS

2013/0082814 A1* 4/2013 Markowski et al. .......... 336/215

FOREIGN PATENT DOCUMENTS

| JP | 59-065865 A   | 4/1984 |
| JP | 63-179378 A   | 7/1988 |
| JP | 08-097036 A   | 4/1996 |
| JP | 08-123188 A   | 5/1996 |
| JP | 2000-223316 A | 8/2000 |
| JP | 2001-165910 A | 6/2001 |
| JP | 2008-140846 A | 6/2008 |
| JP | 2012-013635 A | 1/2012 |

OTHER PUBLICATIONS

Office Action mailed by the Japan Patent Office on Oct. 7, 2014 in the corresponding Japanese patent application No. 2012-229449—7 pages.

* cited by examiner

*Primary Examiner* — Bot Ledynh
(74) *Attorney, Agent, or Firm* — Knobbe, Martens, Olson & Bear LLP (57) ABSTRACT

A differential transformer type magnetic sensor includes a drive coil, a reference coil, and a detection coil. These coils are formed by repeating a linear pattern that is formed on the first surface, penetrates the board, is formed on the second surface, penetrates the board, and returns to the first surface. The reference coil is disposed at a side of one end of the drive coil, and the detection coil is disposed at a side of the other end of the drive coil. Induced current flows to each of the reference coil and the detection coil due to magnetic flux generated as drive current flows to the drive coil. The reference coil and the detection coil are electrically connected so that a direction of the induced current flowing along the reference coil and a direction of the induced current flowing along the detection coil are opposite to each other.

6 Claims, 12 Drawing Sheets

DIFFERENTIAL TRANSFORMER TYPE MAGNETIC SENSOR AND IMAGE FORMING APPARATUS

INCORPORATION BY REFERENCE

This application claims priority to Japanese Patent Application No. 2012-229499 filed on Oct. 17, 2012, the entire contents of which are incorporated by reference herein.

BACKGROUND

The present disclosure relates to a differential transformer type magnetic sensor and an image forming apparatus that detects a residual quantity of toner contained in a development part using the magnetic sensor.

In image forming apparatuses using toner as a developer, a magnetic sensor is used for detection of a residual quantity or a density of the toner. There are various types of magnetic sensors. A differential transformer type magnetic sensor has a configuration in which a drive coil, a differential coil functioning as a detection coil, and another differential coil functioning as a reference coil are disposed on the same core.

As the coils are formed into planar coils, the differential transformer type magnetic sensor can be made compact. As the differential transformer type magnetic sensor using the planar coils, a magnetic sensor in which a first coil (drive coil), a second coil (differential coil), a third coil (differential coil), and a fourth coil (drive coil) are disposed on a first layer, a second layer, a third layer, and a fourth layer respectively, and in which an insulating board is disposed between the neighboring layers is known.

SUMMARY

Technology that further improves the aforementioned technology is proposed as one aspect of the present disclosure.

A differential transformer type magnetic sensor according to one aspect of the present disclosure includes a board, a reference coil, a detection coil, and a drive coil.

The board includes a first surface and a second surface located on the opposite side of the first surface.

The reference coil is formed by repeating a first linear pattern that is formed on the first surface, penetrates the board, is formed on the second surface, penetrates the board, and returns to the first surface.

The detection coil is formed by repeating a second linear pattern that is formed on the first surface, penetrates the board, is formed on the second surface, penetrates the board, and returns to the first surface.

The drive coil is formed by repeating a third linear pattern that is formed on the first surface, penetrates the board, is formed on the second surface, penetrates the board, and returns to the first surface.

The reference coil is disposed at a side of one end of the drive coil, and the detection coil is disposed at a side of the other end of the drive coil.

Induced current flows to each of the reference coil and the detection coil due to magnetic flux generated as drive current flows to the drive coil.

The reference coil and the detection coil are electrically connected so that a direction of the induced current flowing along the reference coil and a direction of the induced current flowing along the detection coil are opposite to each other.

Further, an image forming apparatus according to another aspect of the present disclosure is equipped with the differential transformer type magnetic sensor. The differential transformer type magnetic sensor provides an output corresponding to a height of toner contained in a development part.

DETAILED DESCRIPTION

Hereinafter, a differential transformer type magnetic sensor and an image forming apparatus according to an embodiment in an aspect of the present disclosure will be described with reference to the drawings.

Figure 1:
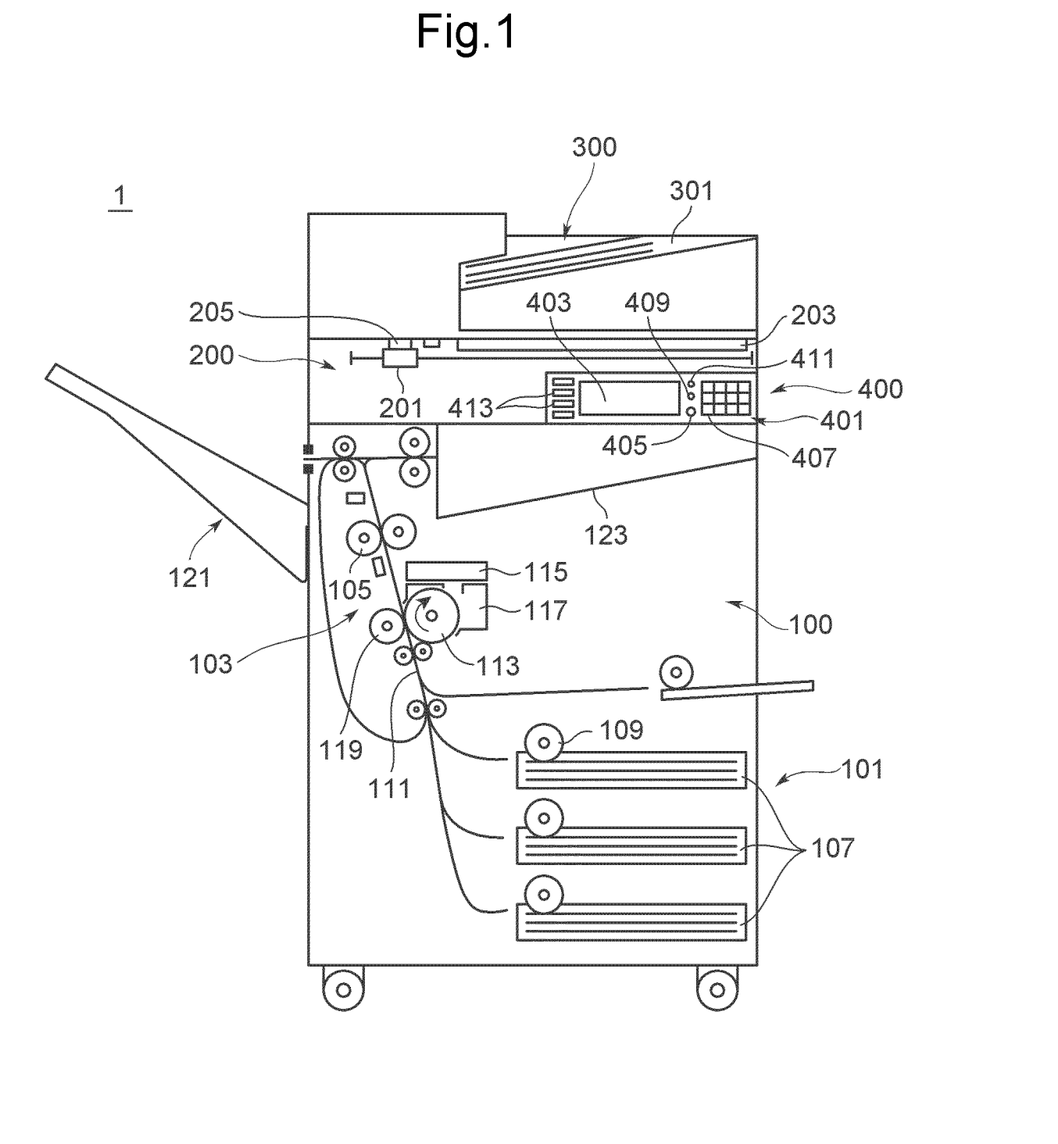
FIG. 1 is a diagram showing a schematic internal structure of an image forming apparatus according to the present embodiment.

FIG. 1 is a diagram showing a schematic internal structure of an image forming apparatus 1 according to an embodiment of the present disclosure. The image forming apparatus 1 may be applied to a digital multifunction device having, for instance, a copy function, a printer function, a scanner function, and a facsimile function. The image forming apparatus 1 includes an apparatus main body 100, a document scanning unit 200 disposed on the apparatus main body 100, a document feeding unit 300 disposed on the document scanning unit 200, and an operating unit 400 disposed in the front of an upper portion of the apparatus main body 100.

The document feeding unit 300 functions as an auto document feeder, and can send a plurality of documents placed on a document loading part 301 so as to be continuously scanned by the document scanning unit 200.

The document scanning unit 200 includes a carriage 201 on which an exposure lamp is mounted, a platen 203 made up of a transparent member such as glass, a charge coupled device (CCD) sensor (not shown), and a document scanning slit 205. When the document loaded on the platen 203 is scanned, the document is scanned by the CCD sensor while the carriage 201 is moved in a longitudinal direction of the platen 203. In contrast, when the document fed from the document feeding unit 300 is scanned, the carriage 201 is moved to a position opposite to the document scanning slit 205, and the document sent from the document feeding unit 300 is scanned through the document scanning slit 205 by the CCD sensor. The CCD sensor outputs the scanned document as image data.

The apparatus main body 100 includes a paper storage unit 101, an image forming unit 103, and a fixing unit 105. The paper storage unit 101 is disposed at a lowest portion of the apparatus main body 100 and includes paper trays 107, each of which can store a stack of paper. In the stack of paper stored in each paper tray 107, the topmost paper is sent toward the paper conveyance path 111 by driving of a pickup roller 109. The paper is conveyed to the image forming unit 103 through the paper conveyance path 111.

The image forming unit 103 forms a toner image on the conveyed paper. The image forming unit 103 includes a photosensitive drum 113, an exposure part 115, a development part 117, and a transfer part 119. The exposure part 115 generates light modulated in response to image data (image data output from the document scanning unit 200, image data transmitted from a personal computer, facsimiled image data, etc.), and scans a circumferential surface of the photosensitive drum (image carrier) 113 charged uniformly. Thereby, an electrostatic latent image corresponding to the image data is formed on the circumferential surface of the photosensitive drum 113. In this state, the toner is supplied from the development part 117 to the circumferential surface of the photosensitive drum 113. Thereby, a toner image corresponding to the image data is formed on the circumferential surface of the photosensitive drum 113. This toner image is transferred to the paper, which is conveyed from the paper storage unit 101 described above, by the transfer part 119.

The paper to which the toner image is transferred is sent to the fixing unit 105. In the fixing unit 105, heat and pressure are applied to the toner image and the paper, and the toner image is fixed to the paper. The paper is ejected to a stack tray 121 or an eject tray 123. In this way, the image forming apparatus 1 prints a monochromic image.

The operating unit 400 includes an operation key part 401 and a display part 403. The display part 403 has a touch panel function, and a screen including a soft key is displayed. A user operates the soft key while watching the screen, thereby performing a setting required to carry out a function such as copying.

The operation key part 401 is provided with operation keys made up of hard keys. In detail, a start key 405, a numeric keypad 407, a stop key 409, a reset key 411, and a function switching key 413 for switching the copy, the printer, the scanner, and the facsimile are provided.

The start key 405 is a key that initiates an operation such as copying or facsimile transmission. The numeric keypad 407 is a keypad that inputs numbers such as the number of copies or a facsimile number. The stop key 409 is a key that stops, for instance, a copy operation midway. The reset key 411 is a key that returns set contents to a default state.

The function switching key 413 includes a copy key and a transmission key, and is a key that mutually switches a copying function and a transmission function. When the copy key is operated, an initial screen for copying is displayed on the display part 403. When the transmission key is operated, an initial screen for facsimile transmission and mail transmission is displayed on the display part 403.

Figure 2:
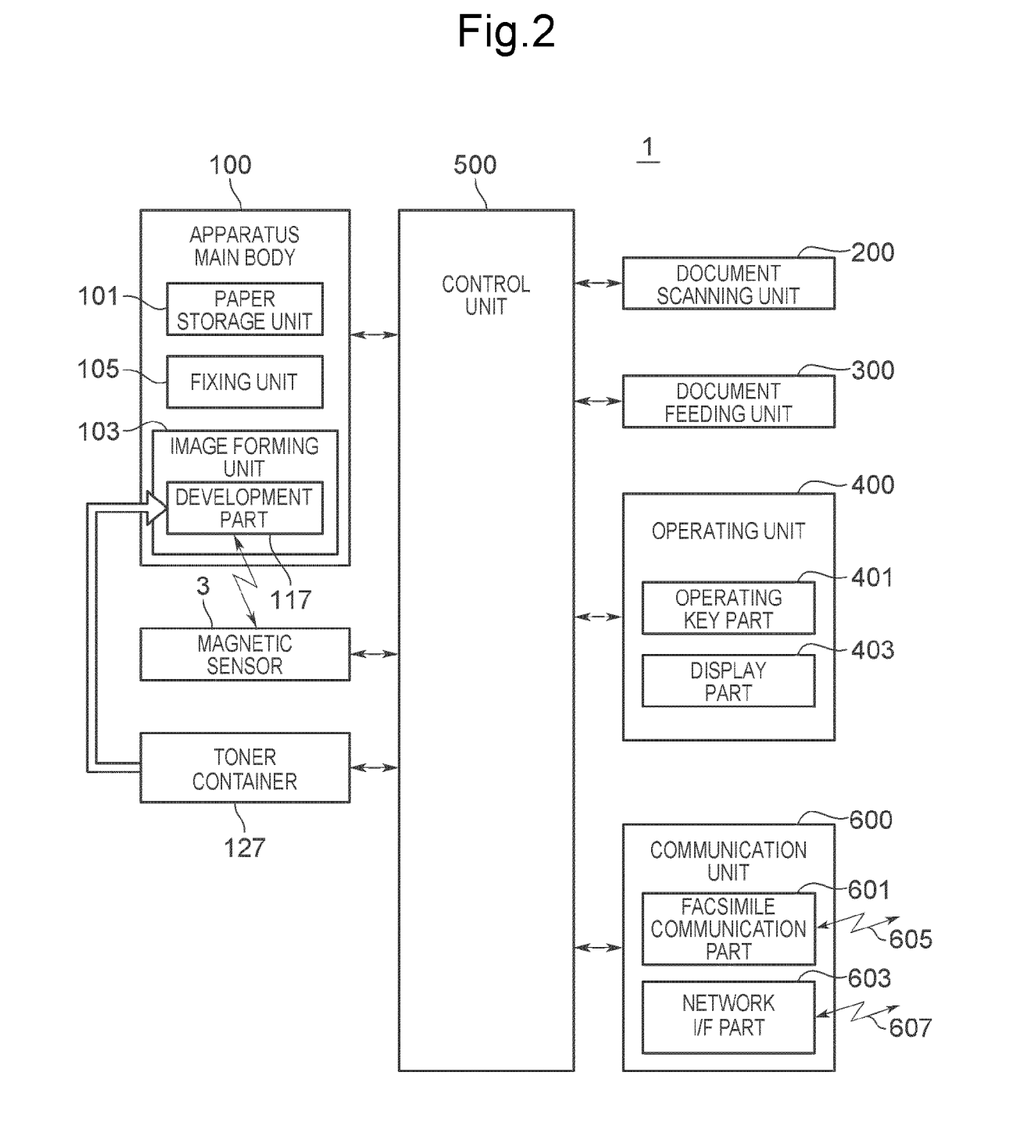
FIG. 2 is a block diagram showing a configuration of the image forming apparatus shown in FIG. 1.

FIG. 2 is a block diagram showing a configuration of the image forming apparatus 1 shown in FIG. 1. The image forming apparatus 1 has a configuration in which the apparatus main body 100, the differential transformer type magnetic sensor 3, the toner container 127, the document scanning unit 200, the document feeding unit 300, the operating unit 400, a control unit 500, and a communication unit 600 are mutually connected by buses. Since the apparatus main body 100, the document scanning unit 200, the document feeding unit 300, and the operating unit 400 have already been described, a description thereof will be omitted.

Toner (magnetic one-component developer) is contained in the toner container 127, and is supplied from the toner container 127 to the development part 117.

The differential transformer type magnetic sensor 3 is the differential transformer type magnetic sensor according to one embodiment of the present disclosure, provides an output corresponding to a height of the toner in the development part 117, and measures a residual quantity of the toner contained in the development part 117 based on the output. The differential transformer type magnetic sensor 3 will be described in detail below.

The control unit 500 includes a central processing unit (CPU), a read only memory (ROM), a random access memory (RAM), and an image memory. The CPU carries out control required to operate the image forming apparatus 1 on the aforementioned components of the image forming apparatus 1 including the apparatus main body 100. The ROM stores software required to control the operation of the image forming apparatus 1. The RAM is used to temporarily store data generated during execution of the software and to store application software. The image memory temporarily stores image data (image data output from the document scanning unit 200, image data sent from the personal computer, facsimiled image data, etc.).

The communication unit 600 includes a facsimile communication part 601 and a network interface (I/F) part 603. The facsimile communication part 601 includes a network control unit (NCU) that controls connection of a phone line with a counterpart facsimile and a modulation and demodulation circuit that modulates and demodulates a signal for facsimile communication. The facsimile communication part 601 is connected to a phone line 605.

The network I/F part 603 is connected to a local area network (LAN) 607. The network I/F part 603 is a communication interface circuit for conducting communication between the LAN 607 and a terminal device such as a personal computer connected to the LAN 607.

Figure 3:
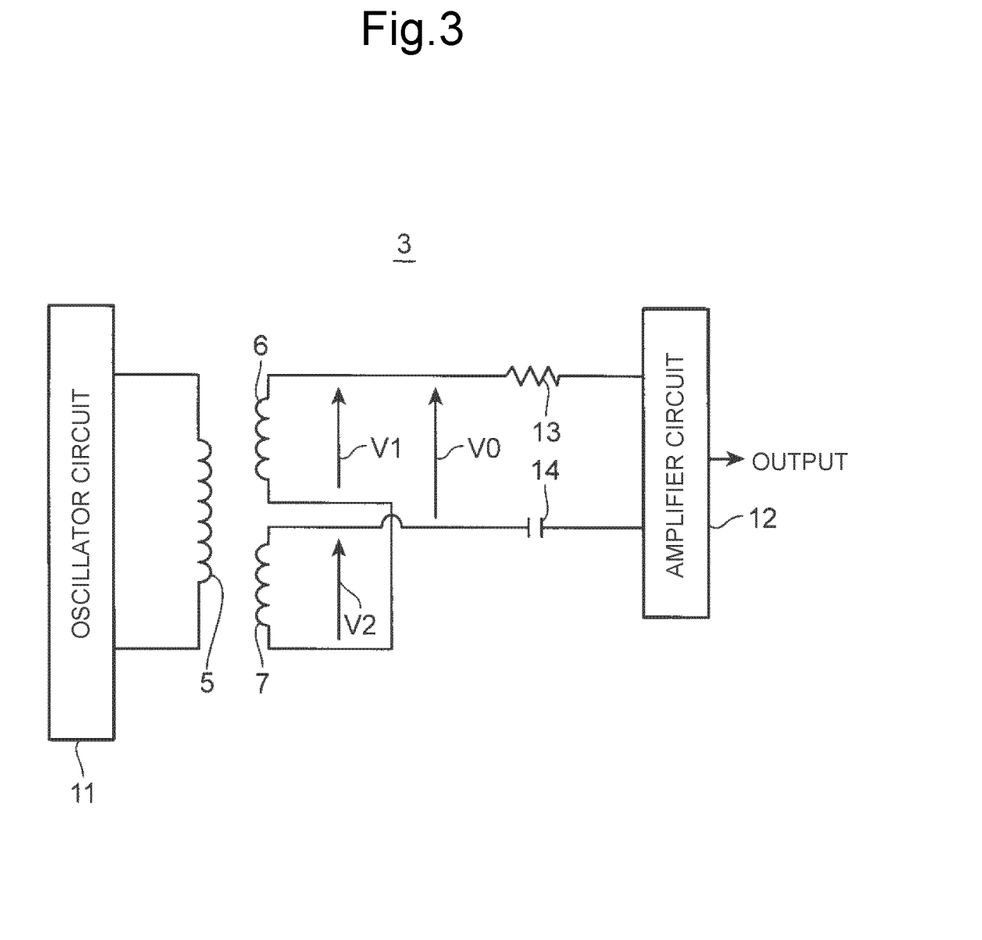
FIG. 3 is a circuit diagram of a differential transformer type magnetic sensor according to the present embodiment.

FIG. 3 is a circuit diagram of the differential transformer type magnetic sensor 3 (which may hereinafter be referred to as a "magnetic sensor 3") according to the present embodiment. The differential transformer type magnetic sensor 3 includes a drive coil 5, a reference coil 6, a detection coil 7, an oscillator circuit 11, an amplifier circuit 12, a resistor 13, and a capacitor 14.

The oscillator circuit 11 generates a high-frequency drive current that drives the drive coil 5.

The reference coil 6 and the detection coil 7 are magnetically coupled with the drive coil 5. The reference coil 6 and the detection coil 7 are differentially connected in series. In other words, the reference coil 6 and the detection coil 7 are electrically connected so that directions of induced currents flowing along the reference coil 6 and the detection coil 7 are opposite to each other. Thereby, a differential voltage V0 (=an electromotive voltage V1 of the reference coil 6 minus an electromotive voltage V2 of the detection coil 7) is input to the amplifier circuit 12.

The other end of the reference coil 6 is connected to the amplifier circuit 12 via the resistor 13, and the other end of the detection coil 7 is connected to the amplifier circuit 12 via the capacitor 14. The resistor 13 is connected to a base of a bipolar transistor within the amplifier circuit 12, and is used to set a gain of the amplifier circuit 12.

The capacitor 14 functions to cut off a direct current component of the differential voltage V0. Thereby, only an alternate current component of the differential voltage V0 is input to the amplifier circuit 12.

An operation of the magnetic sensor 3 will be briefly described. When a drive current generated by the oscillator circuit 11 flows to the drive coil 5, the electromotive voltage V1 is generated at the reference coil 6, and the electromotive voltage V2 is generated at the detection coil 7. When toner is present in the vicinity of the detection coil 7, the electromotive voltage V2 is higher than the electromotive voltage V1. As such, the differential voltage V0 does not become 0 V. The differential voltage V0 is amplified by the amplifier circuit 12, and using a signal that is output from the amplifier circuit 12, a residual quantity of the toner is detected.

Figure 4:
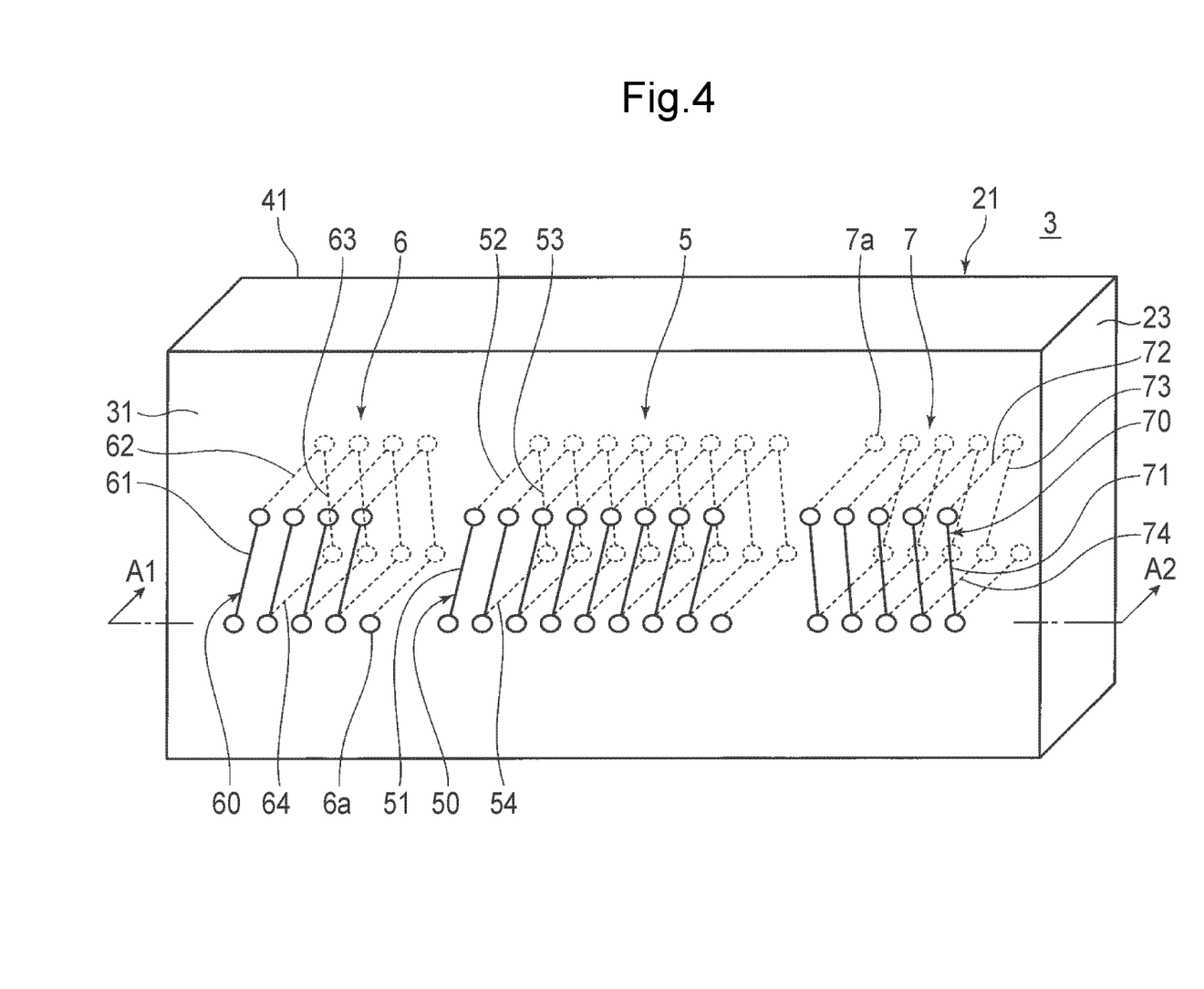
FIG. 4 is a cubic diagram of the differential transformer type magnetic sensor according to the present embodiment.

Next, a structure of the differential transformer type magnetic sensor 3 will be described. FIG. 4 is a cubic diagram of the differential transformer type magnetic sensor 3. The magnetic sensor 3 includes a board 21, the drive coil 5, the reference coil 6, and the detection coil 7. The board 21 is an insulating single-layer printed circuit board. The board 21 includes a first surface 31 and a second surface 41 located on the opposite side of the first surface 31.

Figure 5:
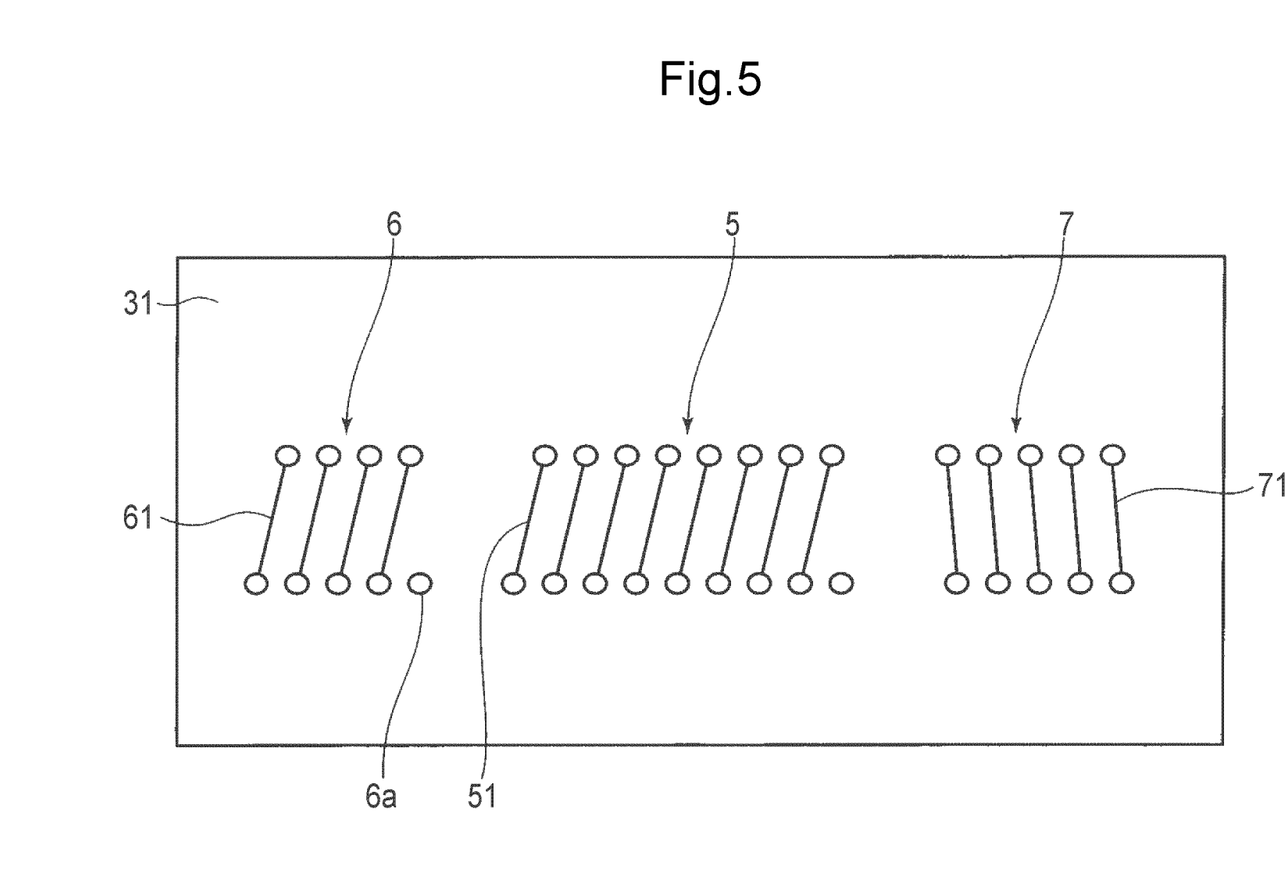
FIG. 5 is a plan view of a first surface of a board.
Figure 6:
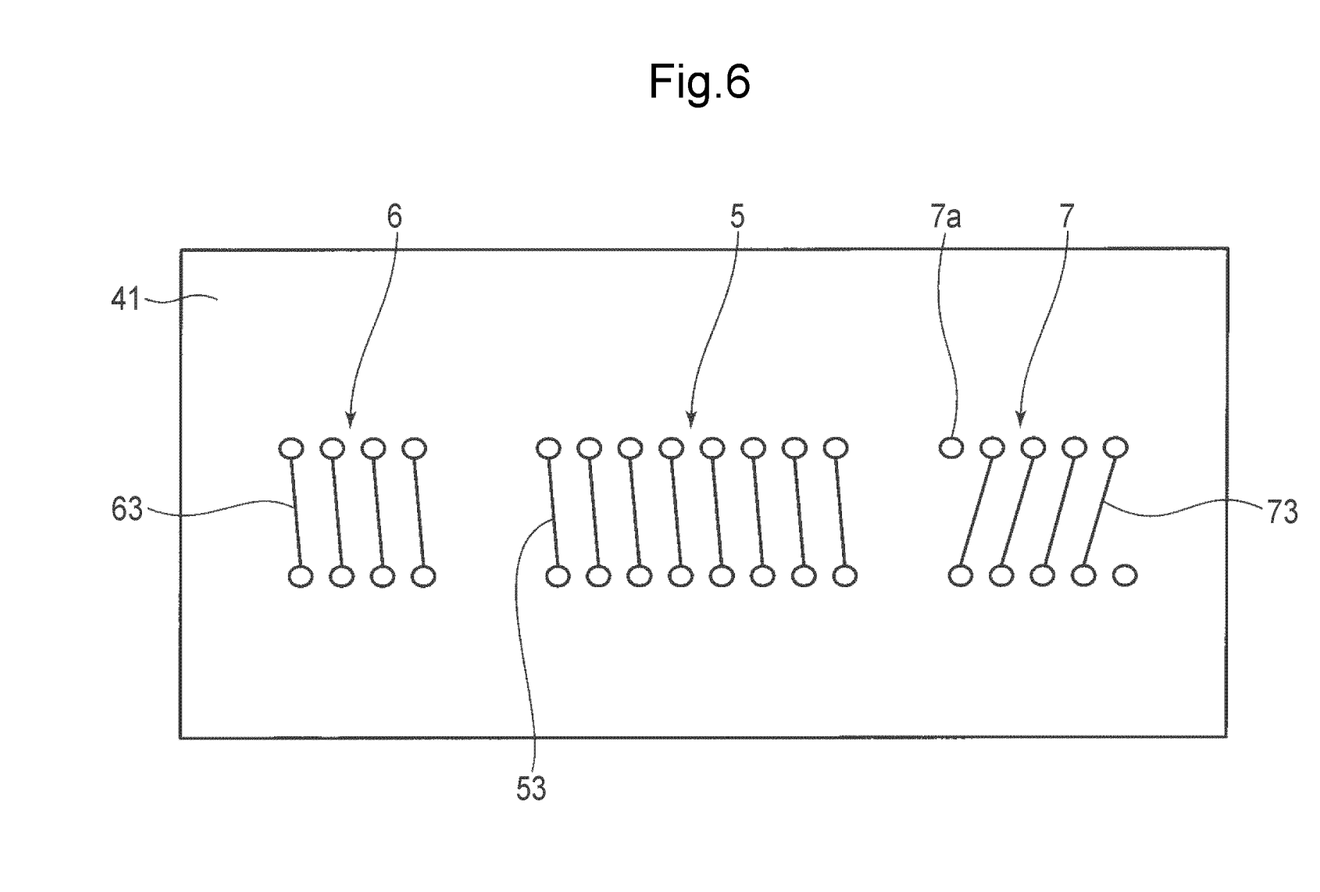
FIG. 6 is a plan view seeing through a second surface of the board from a side of the first surface.
Figure 7:
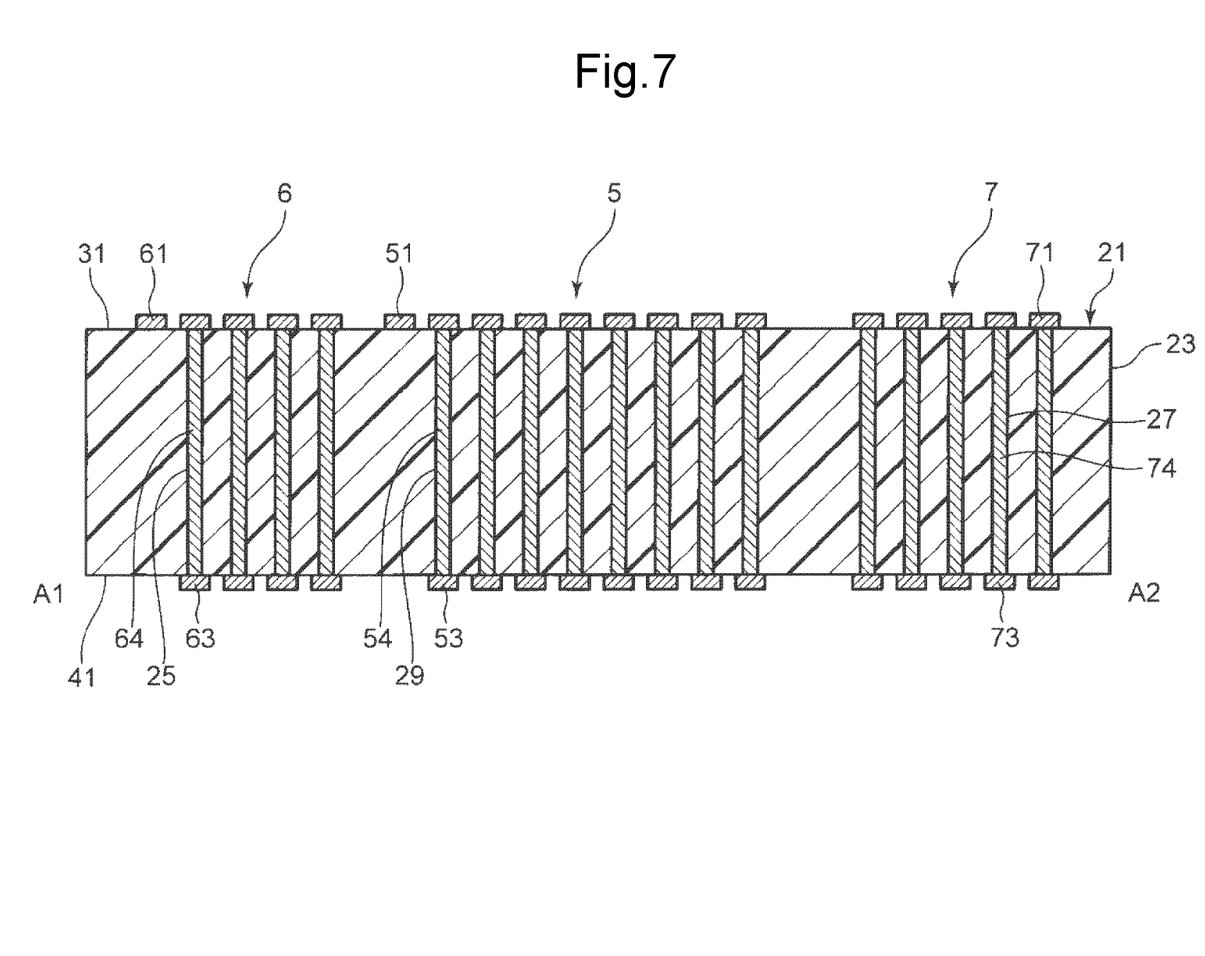
FIG. 7 is a cross-sectional view obtained by cutting the board shown in FIG. 4 along line A1-A2.

FIG. 5 is a plan view of the first surface 31. FIG. 6 is a plan view of the second surface 41 from a side of the first surface 31. FIG. 7 is a cross-sectional view obtained by cutting the board 21 shown in FIG. 4 along line A1-A2.

The reference coil 6 will be described. Referring to FIGS. 4 to 7, the reference coil 6 is a three-dimensional coil obtained by repetitively forming a first linear pattern 60 that is formed on the first surface 31, penetrates the board 21, is formed on the second surface 41, penetrates the board 21, and returns to the first surface 31.

The first linear pattern 60 is a rectangular conductor pattern that has short side portions 61 and 63 and long side portions 62 and 64 longer than the short side portions when viewed from a direction in which the reference coil 6, the drive coil 5, and the detection coil 7 are arranged.

The short side portions 61 are formed on the first surface 31. The long side portions 62 are connected to the short side portions 61 and are buried in hole portions (not shown) passing through the board 21. The short side portions 63 are connected to the long side portions 62 and are formed on the second surface 41. The long side portions 64 are connected to the short side portions 63 and are buried in hole portions 25 passing through the board 21. These hole portions and hole portions to be described below are through-holes formed in the board 21.

The detection coil 7 will be described. Referring to FIGS. 4 to 7, the detection coil 7 is a three-dimensional coil obtained by repetitively forming a second linear pattern 70 that is formed on the first surface 31, penetrates the board 21, is formed on the second surface 41, penetrates the board 21, and returns to the first surface 31.

The second linear pattern 70 is a rectangular conductor pattern that has short side portions 71 and 73 and long side portions 72 and 74 longer than the short side portions when viewed from a direction in which the reference coil 6, the drive coil 5, and the detection coil 7 are arranged.

The short side portions 71 are formed on the first surface 31. The long side portions 72 are connected to the short side portions 71 and are buried in hole portions (not shown) passing through the board 21. The short side portions 73 are connected to the long side portions 72 and are formed on the second surface 41. The long side portions 74 are connected to the short side portions 73 and are buried in hole portions 27 passing through the board 21.

The drive coil 5 will be described. Referring to FIGS. 4 to 7, the drive coil 5 is a three-dimensional coil obtained by repetitively forming a third linear pattern 50 that is formed on the first surface 31, penetrates the board 21, is formed on the second surface 41, penetrates the board 21, and returns to the first surface 31.

The third linear pattern 50 is a rectangular conductor pattern that has short side portions 51 and 53 and long side portions 52 and 54 longer than the short side portions when viewed from a direction in which the reference coil 6, the drive coil 5, and the detection coil 7 are arranged.

The short side portions 51 are formed on the first surface 31. The long side portions 52 are connected to the short side portions 51 and are buried in hole portions (not shown) passing through the board 21. The short side portions 53 are connected to the long side portions 52 and are formed on the second surface 41. The long side portions 54 are connected to the short side portions 53 and are buried in hole portions 29 passing through the board 21.

The drive coil 5 is disposed between the reference coil 6 and the detection coil 7. To be specific, the reference coil 6 is disposed at a side of one end of the drive coil 5, and the detection coil 7 is disposed at a side of the other end of the drive coil 5. The reference coil 6, the drive coil 5, and the detection coil 7 are arranged so that a central portion of the reference coil 6, a central portion of the drive coil 5, and a central portion of the detection coil 7 are located in a straight line.

Due to magnetic flux generated as drive current flows to the drive coil 5, induced current flows to each of the reference coil 6 and the detection coil 7.

One end 6a of the reference coil 6 formed on the first surface 31 and one end 7a of the detection coil 7 formed on the second surface 41 are electrically connected by wiring (not shown). Thereby, the reference coil 6 and the detection coil 7 are electrically connected so that a direction of the induced current along the reference coil 6 and a direction of the induced current along the detection coil 7 are opposite.

Sizes (rectangular sizes) of the first linear pattern 60, the second linear pattern 70, and the third linear pattern 50 are identical to one another. Accordingly, each of the reference coil 6, the detection coil 7, and the drive coil 5 is a rectangular coil that is wound with the same rectangular dimensions and extends in a direction perpendicular to a lateral face 23.

Figure 8:
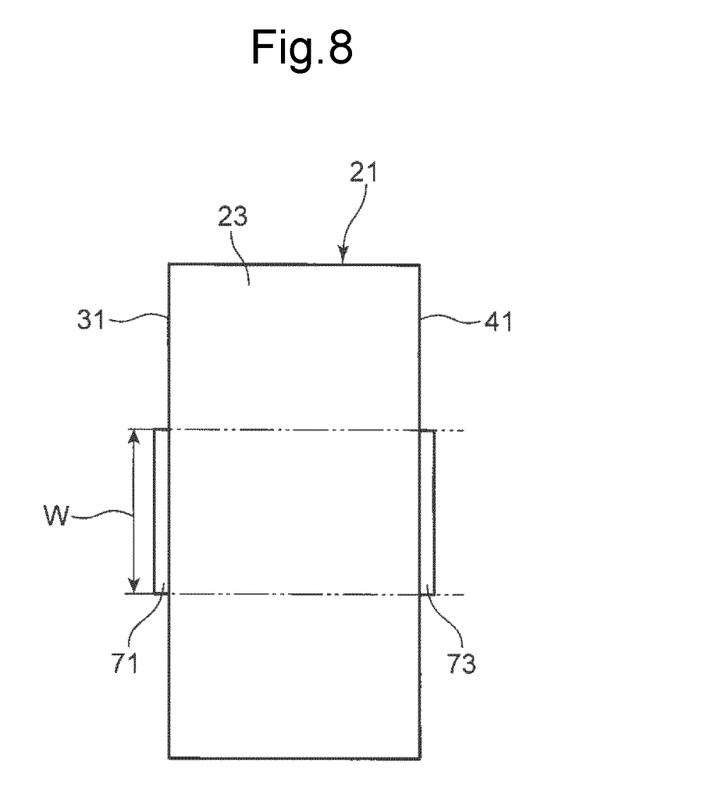
FIG. 8 is a plan view of a lateral face that becomes a detection face of a height of toner among the lateral faces of the board.

FIG. 8 is a plan view of the lateral face 23 that becomes a detection face of the height of the toner among the lateral faces of the board 21. The detection face is the lateral face of a side at which the detection coil 7 is disposed. Referring to FIGS. 4 and 8, directions of the short side portions 61 and 63 of the first linear pattern 60, the short side portions 71 and 73 of the second linear pattern 70, and the short side portions 51 and 53 of the third linear pattern 50 are the same as a direction of a detection width W of the height of the toner. Directions of the long side portions 62 and 64 of the first linear pattern 60, the long side portions 72 and 74 of the second linear pattern 70, and the long side portions 52 and 54 of the third linear pattern 50 are the same as a direction of a thickness of the board 21.

Figure 9:
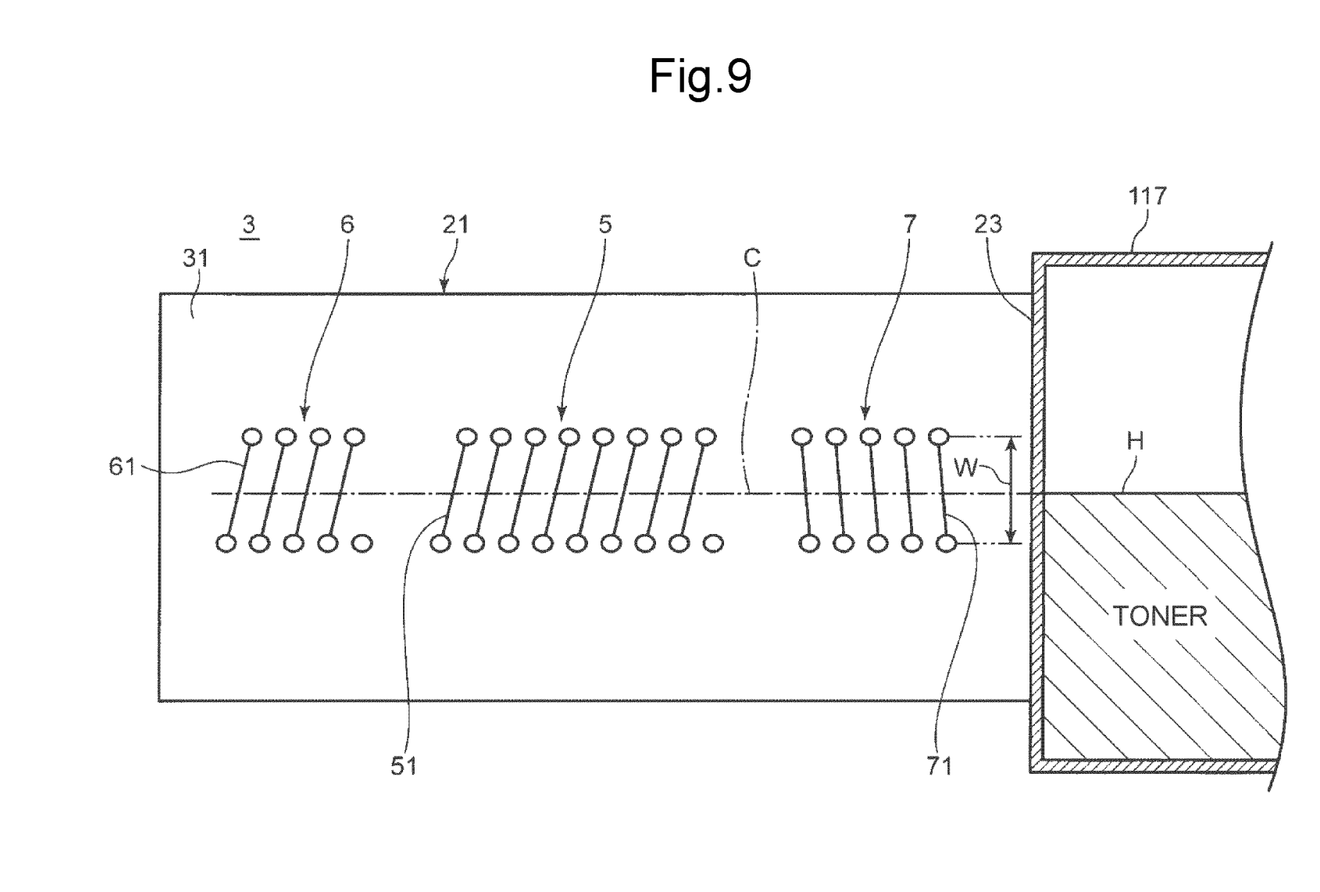
FIG. 9 is a front view of the differential transformer type magnetic sensor according to the present embodiment which is mounted on the development part.
Figure 10:
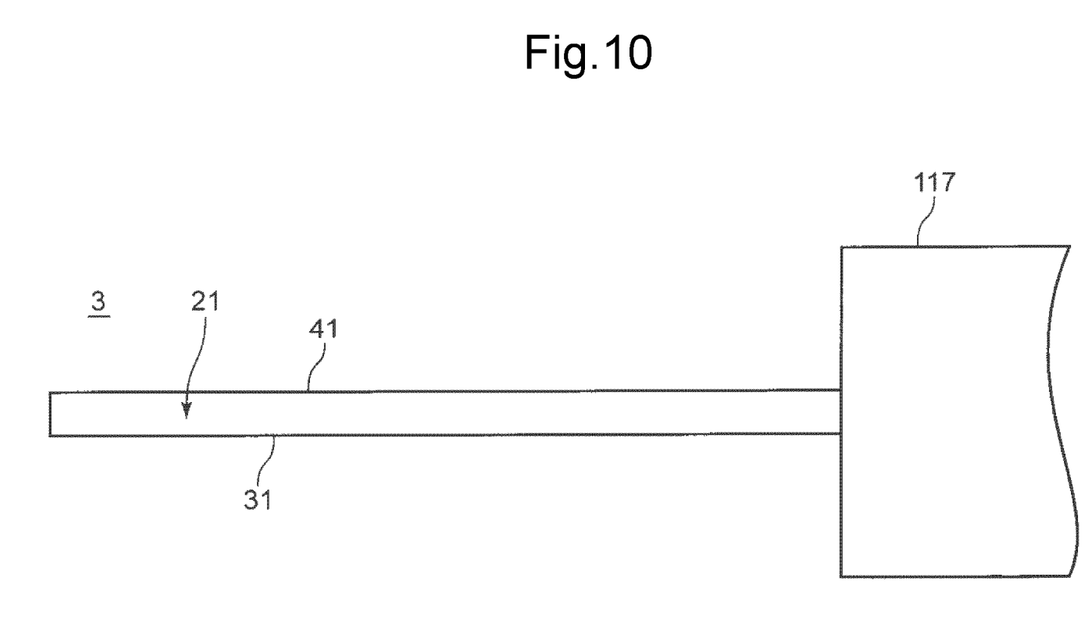
FIG. 10 is a top view of the differential transformer type magnetic sensor according to the present embodiment which is mounted on the development part.

FIG. 9 is a front view of the differential transformer type magnetic sensor 3 mounted on the development part 117. In FIG. 9, the differential transformer type magnetic sensor 3 is shown in a plan view, and the development part 117 is shown in a partial cross-sectional view. FIG. 10 is a top view of the differential transformer type magnetic sensor 3 mounted on the development part 117. Referring to FIGS. 9 and 10, the magnetic sensor 3 is mounted on the development part 117 by bringing the lateral face 23 serving as the detection face into contact with an outer lateral face of a cabinet of the development part 117. Thereby, the differential transformer type magnetic sensor 3 is disposed on the development part 117 with the detection coil 7 directed to the side of the development part 117 and with the reference coil 6 directed to the opposite side of the development part 117. The direction of the short side portions 71 is set to the direction of the height of the toner (one-component developer) contained in the development part 117.

A line indicated by a symbol H denotes a reference height of the toner contained in the development part 117. The magnetic sensor 3 is disposed on the outer lateral face of the cabinet of the development part 117 so that a central portion C of each of the reference coil 6, the drive coil 5, and the detection coil 7 is located at a position of the reference height H. Here, the reference height of the toner refers to a height that becomes a reference when a residual quantity of the toner contained in the development part is detected. For example, a height that is located in the middle of a range of the height of the toner which is to be controlled by the image forming apparatus 1 becomes the reference height of the toner. Further, the expression "the central portion C is located at the position of the reference height H" means that the reference height H is located on a virtual straight line passing through the central portion of the reference coil 6, the central portion of the drive coil 5, and the central portion of the detection coil 7.

Figure 11:
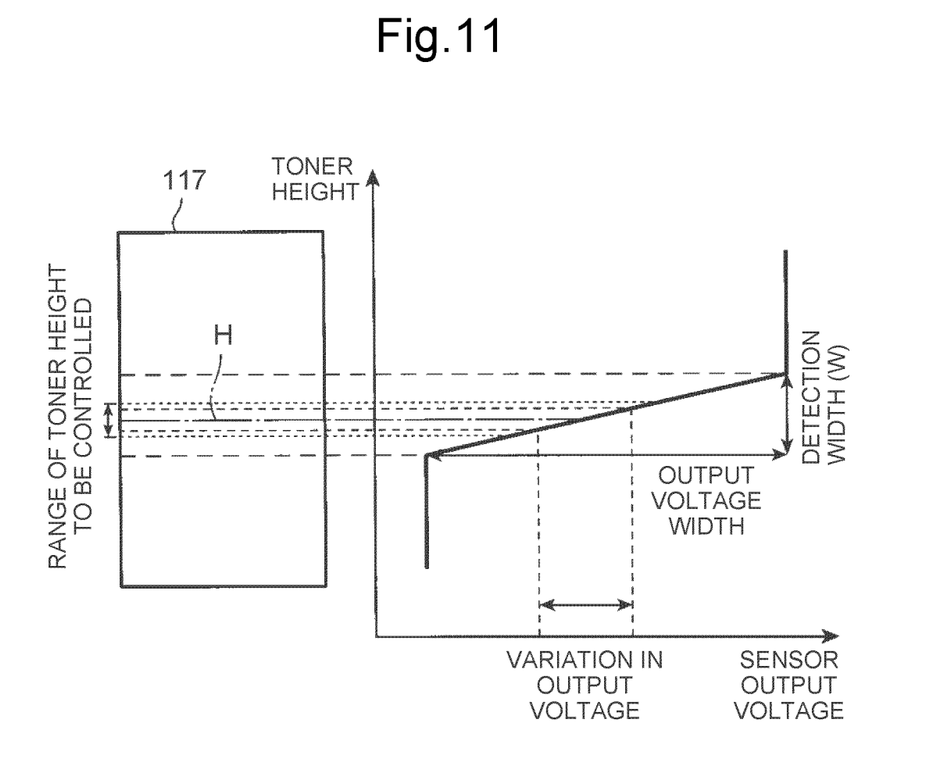
FIG. 11 is a graph showing a relation between an output voltage of the differential transformer type magnetic sensor provided for the image forming apparatus according to the present embodiment and a height of toner contained in the development part.
Figure 12:
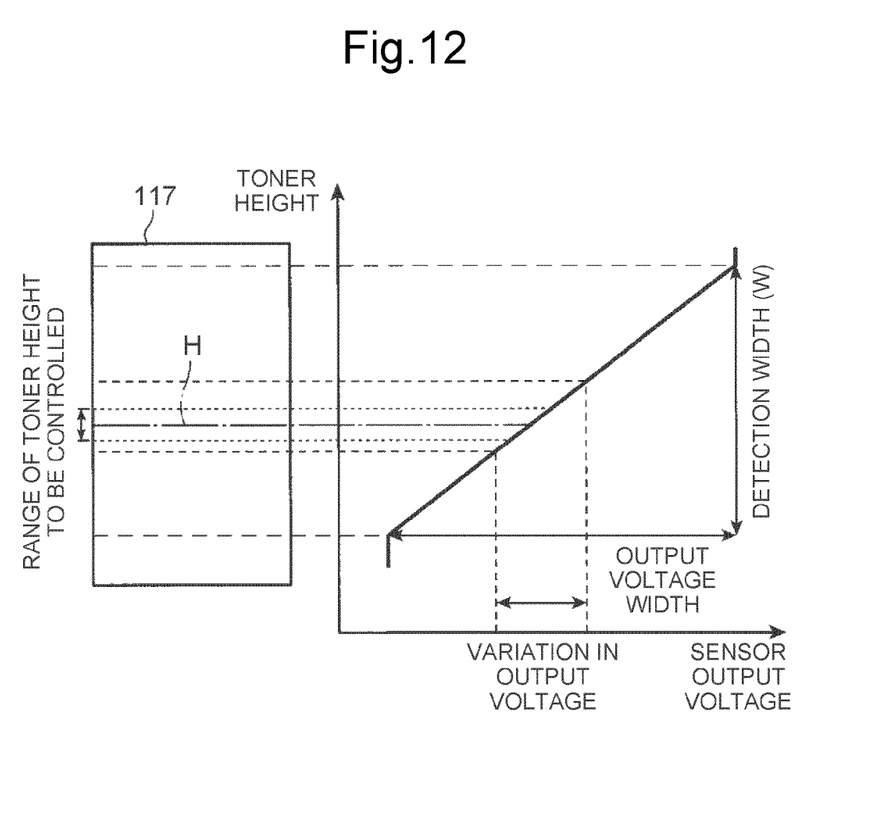
FIG. 12 is a graph showing a relation between an output voltage of a differential transformer type magnetic sensor according to a comparative example and a height of toner contained in a development part.

In the image forming apparatus 1 according to the present embodiment, it is possible to improve precision with which a small change in quantity of the toner contained in the development part 117 is detected. This will be described using FIGS. 11 and 12. FIG. 11 is a graph showing a relation between the output voltage of the differential transformer type magnetic sensor 3 provided for the image forming apparatus 1 according to the present embodiment and the height of the toner contained in the development part 117. FIG. 12 is a graph showing a relation between the output voltage of the differential transformer type magnetic sensor according to a comparative example and the height of the toner contained in the development part 117. The magnetic sensor according to the comparative example is different from that of the present embodiment shown in FIG. 9, and is mounted on the outer lateral face of the cabinet of the development part 117 with the direction of the long side portions 72 and 74 set to the direction of the height of the toner contained in the development part 117.

The horizontal axis of the graph shown in FIGS. 11 and 12 denotes the output voltage of the sensor, and the vertical axis denotes the height of the toner. The height of the toner is, in other words, the residual quantity of the toner contained in the development part 117.

The reference height H (FIG. 9) of the toner, the range of the height of the toner which is to be controlled, an output voltage width of the magnetic sensor, and a variation in output voltage of the magnetic sensor are the same in both the present embodiment shown in FIG. 11 and the comparative example shown in FIG. 12. The output voltage width is a width between the minimum value and the maximum value of the output voltage. The variation in output voltage occurs due to a temperature of a place at which the magnetic sensor is disposed.

In the case of the same output voltage width of the sensor, the narrower the detection width W of the height of the toner becomes, the greater the change in the output voltage becomes with respect to the change in the height of the toner contained in the development part 117. For this reason, as the detection width becomes narrower, sensitivity of the sensor to the small change in the height of the toner contained in the development part 117 can be increased. As such, it is possible to improve the precision with which the small change in the height of the toner contained in the development part (i.e., the small change in the quantity of the toner contained in the development part) is detected.

In the present embodiment, each of the reference coil 6, the detection coil 7, and the drive coil 5 is three-dimensionally formed on the board 21. Even when the number of turns in these coils is increased to secure the sensor output, the detection width W is not widened like a planar coil. Accordingly, according to the present embodiment, since the detection width W can be narrowed, it is possible to improve the precision with which the small change in the quantity of the toner contained in the development part is detected.

Further, in the present embodiment, the height of the toner is detected with the direction of the short side portions 71 and 73 shown in FIG. 4 set to the direction of the height of the toner contained in the development part 117. In the comparative example, the height of the toner is detected with the direction of the long side portions 72 and 74 shown in FIG. 4 set to the direction of the height of the toner contained in the development part 117. For this reason, with regard to the detection width W of the height of the toner, the present embodiment is narrower than the comparative example. Since the output voltage width of the present embodiment is equal to that of the comparative example, a change in output voltage of the sensor with respect to a change in height of the toner is greater in the present embodiment than in the comparative example. Accordingly, the present embodiment can improve the precision with which the small change in the quantity of the toner contained in the development part 117 is detected, compared to the comparative example.

As described above, in the comparative example, the change in the output voltage of the sensor with respect to the change in the height of the toner is small. For this reason, in the comparative example, the variation in the output voltage of the sensor cannot be absorbed, and as shown in FIG. 12, the height of the toner is out of the range of the height of the toner which is to be controlled. On the other hand, in the present embodiment, the change in the output voltage of the sensor with respect to the change in the height of the toner is great. For this reason, in the present embodiment, the variation in the output voltage of the sensor can be absorbed, and as shown in FIG. 11, the height of the toner can fall within the range of the height of the toner which is to be controlled.

Further, according to the present embodiment, as shown in FIG. 9, the differential transformer type magnetic sensor 3 is disposed on the development part 117 so that the central portion of each of the reference coil 6, the drive coil 5, and the detection coil 7 is located at the position of the reference height H of the toner contained in the development part 117.

For this reason, in the vicinity of the reference height H of the toner contained in the development part 117, the change in the output voltage of the sensor can be increased with respect to the small change in the height of the toner. Accordingly, while the residual quantity of the toner contained in the development part 117 is controlled to the reference height H, the residual quantity of the toner in the development part 117 can be controlled with high precision when an electrostatic latent image is developed to a toner image.

Furthermore, according to the present embodiment, as shown in FIG. 4, portions of the first linear pattern 60, the second linear pattern 70, and the third linear pattern 50 which are formed on the first surface 31 are the respective short side portions 61, 71, and 51. Portions of the first linear pattern 60, the second linear pattern 70, and the third linear pattern 50 which are formed on the second surface 41 are the respective short side portions 63, 73, and 53. As shown in FIGS. 4 and 7, portions of the first linear pattern 60 which penetrate the board 21 are the long side portions 62 and 64. Portions of the second linear pattern 70 which penetrate the board 21 are the long side portions 72 and 74. Portions of the third linear pattern 50 which penetrate the board 21 are the long side portions 52 and 54.

When the portions of the first linear pattern 60, the second linear pattern 70, and the third linear pattern 50 which penetrate the board 21 are set to the short side portions, in other words, when the direction of the board 21 is set to the direction of the short side portions, the detection width W is limited to the thickness of the board 21, and a degree of freedom for setting a magnitude of the detection width W is lost. According to the present embodiment, the portions of the first linear pattern 60, the second linear pattern 70, and the third linear pattern 50 which are formed on the first surface 31 and the second surface 41 are set to the short side portions. As such, the degree of freedom for setting the magnitude of the detection width W is generated.

Further, in the present embodiment, the drive coil 5, the reference coil 6, and the detection coil 7 are disposed on a piece of the board 21. As such, miniaturization and cost saving of the magnetic sensor 3 are achieved.

When there is a desire to detect the small change in the quantity of the detection target (toner) using the differential transformer type magnetic sensor, and when the residual quantity of the toner contained in the development part is little, a quantity of the toner supplied to the electrostatic latent image is insufficient, and there is a fear of the image becoming blurred. On the other hand, when the residual quantity of the toner contained in the development part is great, the toner is insufficiently charged when agitated and charged. Both of these contribute to a reduction in image quality.

For this reason, a reference quantity of the toner contained in the development part (in other words, the reference height of the toner contained in the development part) is controlled to a preset setting value using the magnetic sensor. To form a high-quality image, an allowable range of the change in the quantity of the toner is narrow. As such, it is necessary to detect the small change in the quantity of the toner contained in the development part.

In contrast, according to the embodiment, since each of the reference coil 6, the detection coil 7, and the drive coil 5 is three-dimensionally formed on the board 21, and the detection width W can be made narrow, it is possible to improve the precision with which the small change in the quantity of the toner contained in the development part is detected.

In the present embodiment, the differential transformer type magnetic sensor 3 has been described as a sensor that detects the residual quantity of the toner in the development part 117 of the image forming apparatus 1 as an example. However, the use of the differential transformer type magnetic sensor provided by the present disclosure is not limited to the detection of the residual quantity of the toner in the development part 117.

The photosensitive drum 113 and the exposure part 115 of FIG. 1 function as a latent image forming part that forms the latent image indicated by the image data. In the present embodiment, the description has been made of the type in which the electrostatic latent image indicated by the image data is formed on the photosensitive drum 113, and this electrostatic latent image is developed by the toner. However, the type of the development is not limited to such a type. A type in which the electrostatic latent image indicated by the image data is formed on the paper, and this electrostatic latent image is developed by the toner may be used, and a type in which the toner is supplied to a magnetic latent image indicated by the image data, and the magnetic latent image is developed may be used.

Various modifications and alterations of this disclosure will be apparent to those skilled in the art without departing from the scope and spirit of this disclosure, and it should be understood that this disclosure is not limited to the illustrative embodiments set forth herein.

What is claimed is:

1. A differential transformer type magnetic sensor comprising:
    a board formed of a printed circuit board that includes a first surface and a second surface located on the opposite side of the first surface;
    a reference coil that is formed as a three-dimensional conductor pattern on the board by repeating a first linear pattern that is formed on the first surface, penetrates the board, is formed on the second surface, penetrates a through-hole formed in the board, and returns to the first surface;
    a detection coil that is formed as a three-dimensional conductor pattern on the board by repeating a second linear pattern that is formed on the first surface, penetrates the board, is formed on the second surface, penetrates a through-hole formed in the board, and returns to the first surface; and
    a drive coil that is formed as a three-dimensional conductor pattern on the board by repeating a third linear pattern that is formed on the first surface, penetrates the board, is formed on the second surface, penetrates a through-hole formed in the board, and returns to the first surface,
    wherein the reference coil is disposed at a side of one end of the drive coil, and the detection coil is disposed at a side of the other end of the drive coil;
    induced current flows to each of the reference coil and the detection coil due to magnetic flux generated as drive current flows to the drive coil;
    the reference coil and the detection coil are electrically connected so that a direction of the induced current flowing along the reference coil and a direction of the induced current flowing along the detection coil are opposite to each other, and thus the differential transformer type magnetic sensor provides an output corresponding a height of toner contained in a development part of an image forming apparatus;
    the reference coil, the drive coil, and the detection coil are arranged so that a central portion of the reference coil, a central portion of the drive coil, and a central portion of the detection coil are located in a straight line; and
    the differential transformer type magnetic sensor is disposed relative to the development part so that the central portion of each of the reference coil, the detection coil, and the drive coil is located at a position of a reference height of the toner contained in the development part.

2. The differential transformer type magnetic sensor according to claim 1, wherein:
    each of the first linear pattern, the second linear pattern, and the third linear pattern is a rectangular conductor pattern that has short side portions and long side portions longer than the short side portions when viewed from a direction in which the reference coil, the drive coil, and the detection coil are arranged; and the differential transformer type magnetic sensor is disposed on the development part with a direction of short side portions in each of the reference coil, the detection coil, and the drive coil set equal to a direction of the height of the toner contained in the development part.

3. The differential transformer type magnetic sensor according to claim 2, wherein:
portions of the first linear pattern, the second linear pattern, and the third linear pattern which are formed on the first surface and the second surface are the short side portions; and
portions of the first linear pattern, the second linear pattern, and the third linear pattern which penetrate the board are the long side portions.

4. An image forming apparatus equipped with a differential transformer type magnetic sensor providing an output corresponding to a height of toner contained in a development part, the differential transformer type magnetic sensor comprising:
a board that includes a first surface and a second surface located on the opposite side of the first surface;
a reference coil that is formed by repeating a first linear pattern that is formed on the first surface, penetrates the board, is formed on the second surface, penetrates the board, and returns to the first surface;
a detection coil that is formed by repeating a second linear pattern that is formed on the first surface, penetrates the board, is formed on the second surface, penetrates the board, and returns to the first surface; and
a drive coil that is formed by repeating a third linear pattern that is formed on the first surface, penetrates the board, is formed on the second surface, penetrates the board, and returns to the first surface,
wherein the reference coil is disposed at a side of one end of the drive coil, and the detection coil is disposed at a side of the other end of the drive coil;
induced current flows to each of the reference coil and the detection coil due to magnetic flux generated as drive current flows to the drive coil; and
the reference coil and the detection coil are electrically connected so that a direction of the induced current flowing along the reference coil and a direction of the induced current flowing along the detection coil are opposite to each other.

5. The image forming apparatus according to claim 4, wherein the differential transformer type magnetic sensor is disposed on the development part with a direction of short side portions in each of the reference coil, the detection coil, and the drive coil set to a direction of the height of the toner contained in the development part.

6. The image forming apparatus according to claim 4, wherein the differential transformer type magnetic sensor is disposed on the development part so that a central portion of each of the reference coil, the detection coil, and the drive coil is located at a position of a reference height of the toner contained in the development part.

* * * * *